(12) United States Patent
Huang et al.

(10) Patent No.: US 10,335,294 B2
(45) Date of Patent: Jul. 2, 2019

(54) SYSTEMS AND METHODS FOR AUTOMATICALLY TUNING POWERED PROSTHESIS IMPEDANCE CONTROL PARAMETERS

(71) Applicant: North Carolina State University, Raleigh, NC (US)

(72) Inventors: He Huang, Cary, NC (US); Ming Liu, Cary, NC (US)

(73) Assignee: North Carolina State University, Raleigh, NC (US)

( * ) Notice: Subject to any disclaimer, the term of this patent is extended or adjusted under 35 U.S.C. 154(b) by 6 days.

(21) Appl. No.: 15/336,854

(22) Filed: Oct. 28, 2016

(65) Prior Publication Data

US 2017/0119551 A1 May 4, 2017

Related U.S. Application Data

(60) Provisional application No. 62/247,553, filed on Oct. 28, 2015.

(51) Int. Cl.
*A61F 2/70* (2006.01)
*A61F 2/60* (2006.01)
(Continued)

(52) U.S. Cl.
CPC .............. *A61F 2/72* (2013.01); *A61B 5/112* (2013.01); *A61B 5/4851* (2013.01); *A61F 2/60* (2013.01);
(Continued)

(58) Field of Classification Search
None
See application file for complete search history.

(56) References Cited

U.S. PATENT DOCUMENTS

2011/0202144 A1 8/2011 Palmer et al.
2013/0173022 A1* 7/2013 Arabian ............... A61F 2/6607
623/49

FOREIGN PATENT DOCUMENTS

WO WO2014/043681 A2 * 3/2014 ............... A61F 2/66
WO 2015038979 A1 3/2015

OTHER PUBLICATIONS

Borjian, et al., "The Design of an Intelligent Mechanical Active Prosthetic Knee", IEEE, 2008, pp. 3016-3021.
(Continued)

*Primary Examiner* — David H Willse
(74) *Attorney, Agent, or Firm* — Meunier Carlin & Curfman LLC

(57) ABSTRACT

An example system for tuning powered prosthesis impedance control parameters can include a powered prosthesis and intelligent tuner operably connected to the powered prosthesis. The powered prosthesis can include a joint, a motor that is mechanically coupled to the joint, a plurality of sensors configured to measure a plurality of gait parameters associated with a subject, and an impedance controller. The motor of the powered prosthesis can be configured to drive the joint, and the impedance controller of the powered prosthesis can be configured to output a control signal for adjusting a torque of the motor, where the torque is adjusted as a function of the measured gait parameters and a plurality of impedance control parameters. The intelligent tuner can be configured to adjust at least one of the impedance control parameters using a rule base.

18 Claims, 18 Drawing Sheets

(51) Int. Cl.
A61F 2/72 (2006.01)
A61F 2/76 (2006.01)
A61B 5/11 (2006.01)
A61F 2/68 (2006.01)
A61B 5/00 (2006.01)
A61F 5/01 (2006.01)
A61F 2/50 (2006.01)

(52) U.S. Cl.
CPC ............... *A61F 2/68* (2013.01); *A61F 2/76* (2013.01); *A61F 2002/5016* (2013.01); *A61F 2002/5036* (2013.01); *A61F 2002/607* (2013.01); *A61F 2002/701* (2013.01); *A61F 2002/704* (2013.01); *A61F 2002/7615* (2013.01); *A61F 2002/7625* (2013.01); *A61F 2002/7645* (2013.01); *A61F 2005/0155* (2013.01)

(56) References Cited

OTHER PUBLICATIONS

Dingwell, et al., "Kinematic variability and local dynamic stability of upper body motions when walking at different speeds", J Biomech, vol. 39, 2006, pp. 444-452.
Fletcher, et al., "Trends in rehabilitation after amputation for geriatric patients with vascular disease: implications for future health resource allocation", Arch Phys Med Rehabil, vol. 83, 2002, pp. 1389-1393.
Granata, et al., "Joint angular velocity in spastic gait and the influence of muscle-tendon lengthening", Bone Joint Surg Am, vol. 82, 2000, pp. 174-186.
Gregg, et al., "Experimental Effective Shape Control of a Powered Transfemoral Prosthesis", IEEE Int Conf Rehabil Robot, 2013, 7 pages.
Gregg, et al., "Virtual Constraint Control of a Powered Prosthetic Leg: From Simulation to Experiments with Transfemoral Amputees", IEEE transactions on robotics, vol. 30, 2014, pp. 1455-1471.
Guillaume, S., "Designing fuzzy inference systems from data: an interpretability-oriented review", IEEE Trans Fuzzy Systems, vol. 9, 2001, pp. 426-443.
Herr, et al., "User-adaptive control of a magnetorheological prosthetic knee", Ind Robot, vol. 30, 2003, pp. 42-55.
Holgate, et al., "A novel control algorithm for wearable robotics using phase plane invariants", Proc IEEE Int Conf Robot Automat, 2009, pp. 3845-3850.
Huang, et al., "A stable self-organizing fuzzy controller for robotic motion control", IEEE Trans Ind Electron, vol. 47, 2000, pp. 421-428.
Kadaba, et al., "Repeatability of kinematic, kinetic, and electromyographic data in normal adult gait", J Orthop Res, vol. 7, 1989, pp. 849-860.
Kearney, et al., "System Identification of Human Joint Dynamics", Crit Rev Biomed Eng, vol. 18, 1990, pp. 55-87.
Lambrecht, et al., "Design of a Semi-Active Knee Prosthesis", IEEE Int Conf Robot Automat, 2009, pp. 639-645.
Lawson, et al., "A powered prosthetic intervention for bilateral transfemoral amputees.", IEEE Trans Biomed Eng, vol. 62, 2015, pp. 1042-1050.
Lenzi, et al., "Minimum jerk swing control allows variable cadence in powered transfemoral prostheses.", Conf Proc IEEE Eng Med Biol Soc, 2014, 4 pages.
Liu, et al., "A Prototype for Smart Prosthetic Legs: Analysis and Mechanical Design", Adv. Mat. Res. , vol. 403-408, 2011, pp. 1999-2006.
Liu, et al., "Improving finite state impedance control of active transfemoral prostheses using Dempster-Shafer state transition rules", J Intell Robot Syst, vol. 76, 2014, pp. 461-474.
Martinez-Villalpando, et al., "Agonist-antagonist active knee prosthesis: A preliminary study in level-ground walking", J Rehabil Res Dev, vol. 46, 2009, pp. 361-373.
Melingui, et al., "Adaptive navigation of an omni-drive autonomous mobile robot in unstructured dynamic environments.", Proc IEEE Int Conf Robot Biomimet, 2013, pp. 1924-1929.
Miller, et al., "The influence of falling, fear of falling, and balance confidence on prosthetic mobility and social activity among individuals with a lower extremity amputation", Arch Phys Med Rehabil, vol. 82, 2001, pp. 1238-1244.
Mirbagheri, et al., "Intrinsic and reflex contributions to human ankle stiffness: variation with activation level and position", Exp Brain Res, vol. 135, 2000, pp. 423-436.
Orendurff, et al., "The effect of walking speed on center of mass displacement", J Rehabil Res Dev, vol. 41, 2004, pp. 829-834.
Pfeifer, et al., "Knee stiffness estimation in physiological gait", Conf Proc IEEE Eng Med Biol Soc, 2014, 4 pages.
Pfeifer, et al., "Model-based estimation of knee stiffness", IEEE Trans Biomed Eng, vol. 59, 2012, pp. 2604-2612.
Rouse, et al., "Estimation of human ankle impedance during the stance phase of walking.", IEEE Trans Neural Syst Rehabil Eng, vol. 22, 2014, pp. 870-878.
Shamaei, et al., "Estimation of quasi-stiffness and propulsive work of the human ankle in the stance phase of walking", PLoS One, vol. 8, 2013, e59935.
Shamaei, et al., "Estimation of quasi-stiffness of the human hip in the stance phase of walking", PLoS One, vol. 8, 2013, e81841.
Shamaei, et al., "Estimation of quasi-stiffness of the human knee in the stance phase of walking", PLoS, vol. One 8, 2013, e59993.
Simon, et al., "Configuring a powered knee and ankle prosthesis for transfemoral amputees within five specific ambulation modes", PloS One, vol. 9, 2014, e99387.
Sup, et al., "Design and control of a powered transfemoral prosthesis", Int J Robot Res, vol. 27, 2008, pp. 263-273.
Sup, et al., "Preliminary Evaluations of a Self-Contained Anthropomorphic Transfemoral Prosthesis", IEEE/ASME transactions on mechatronics, vol. 14, 2009, pp. 667-676.
Torrealba, et al., "Towards the development of knee prostheses: review of current researches", Kybernetes, vol. 37, 2008, pp. 1561-1576.
Tura, et al., "Gait symmetry and regularity in transfemoral amputees assessed by trunk accelerations.", J Neuroeng Rehabil, vol. 7: 4, 2010, 10 pages.
Wang, et al., "Generating fuzzy rules by learning from examples", IEEE Trans Syst Man Cybern, vol. 22, 1992, pp. 1414-1427.
Weiss, et al., "Position dependence of ankle joint dynamics—I., Passive mechanics", J Biomech, vol. 19, 1986, pp. 727-735.
Weiss, et al., "Position dependence of ankle joint dynamics—II., Active mechanics", J Biomech, vol. 19, 1986, pp. 737-751.
Winter, D., "Kinematic and kinetic patterns in human gait: Variability and compensating effects", Hum Movement Sci, vol. 3, 1984, pp. 51-76.
Young, et al., "Voluntarily changing step length or step width affects dynamic stability of human walking", Gait Posture, vol. 35, 2012, pp. 472-477.
Ziegler-Graham, et al., "Estimating the prevalence of limb loss in the United States: 2005 to 2050", Arch Phys Med Rehabi, vol. 1 89, 2008, pp. 422-429.

* cited by examiner

TABLE 1. Initial impedance control parameter extrema values.

| IC parameters | Phases | | | | |
| --- | --- | --- | --- | --- | --- |
| | IDS | SS | TDS | SWF | SWE |
| Stiffness, $k$ (Nm deg$^{-1}$) | | | | | |
|   High | 2.2 | 3.5 | 2.5 | 1.5 | 1.2 |
|   Low | 1.6 | 2.8 | 0.5 | 1.0 | 0.8 |
| Equilibrium position, $\theta_E$ (degrees) | | | | | |
|   High | 10 | 17 | 60 | 70 | 15 |
|   Low | 4 | 10 | 30 | 60 | 5 |
| Damping coefficient, $C$ (Nm deg$^{-1}$) | | | | | |
|   High | 0.1 | 0.3 | 0.06 | 0.06 | 0.06 |
|   Low | 0.01 | 0.01 | 0 | 0 | 0 |

*FIG. 5*

Table A: Fuzzy Rules Used in the Initial Double Stance Phase

| | Input | | | Output | | |
|---|---|---|---|---|---|---|
| | $\Delta\theta_{knee}$ | $\Delta T_{dura}$ | $\Delta T_{dura}$ | $\Delta k$ | $\Delta\theta_E$ | $\Delta C$ |
| 1 | N | N | N | N | N | P |
| 2 | P | N | N | P | P | P |
| 3 | P | P | N | N | P | P |
| 4 | N | P | N | N | N | P |
| 5 | N | N | P | P | N | N |
| 6 | P | N | P | P | P | N |
| 7 | P | P | P | P | P | N |
| 8 | N | P | P | N | N | N |

Note: N: negative and P: positive. Rules are in the form of IF-THEN statement.

*FIG. 6A*

Table B: Fuzzy Rules Used in the Single Stance Phase

| | Input | | | Output | | |
|---|---|---|---|---|---|---|
| | $\Delta\theta_{knee}$ | $\Delta T_{dura}$ | $\Delta T_{dura}$ | $\Delta k$ | $\Delta\theta_E$ | $\Delta C$ |
| 1 | N | N | N | P | N | N |
| 2 | P | N | N | P | P | N |
| 3 | P | P | N | N | P | N |
| 4 | N | P | N | N | N | N |
| 5 | N | N | P | P | N | P |
| 6 | P | N | P | P | P | P |
| 7 | P | P | P | N | P | P |
| 8 | N | P | P | N | N | P |

Note: N: negative and P: positive. Rules are in the form of IF-THEN statement.

*FIG. 6B*

Table C: Fuzzy Rules Used in the Swing Extension Phase

| | Input | | | Output | | |
|---|---|---|---|---|---|---|
| | $\Delta\theta_{knee}$ | $\Delta T_{dura}$ | $\Delta T_{dura}$ | $\Delta k$ | $\Delta\theta_{g}$ | $\Delta C$ |
| 1 | N | N | N | P | N | N |
| 2 | P | N | N | P | P | P |
| 3 | P | P | N | N | P | P |
| 4 | N | P | N | P | N | N |
| 5 | N | N | P | P | N | N |
| 6 | P | N | P | N | P | P |
| 7 | P | P | P | N | P | P |
| 8 | N | P | P | N | N | N |

Note: N: negative and P: positive. Rules are in the form of IF-THEN statement.

*FIG. 6C*

TABLE 2. Comparison of RMS errors at the beginning and end of trials.

| Method | Subject | | | | |
|---|---|---|---|---|---|
| | AB1 | AB2 | TF1 | TF2 |
| HME | | | | |
| t | 2.09 | 2.28 | 2.25 | — |
| p | 0.037 | 0.028 | 0.030 | — |
| CES | | | | |
| t | 7.06 | 3.00 | 3.89 | 8.81 |
| p | <0.001 | 0.006 | 0.003 | 0.001 |
| Non-tuning | | | | |
| t | 0.88 | 0.80 | 0.41 | — |
| p | 0.209 | 0.226 | 0.348 | — |

Statistical comparisons were made within each subject across trials (DF = 7). Bold characters indicate statistical significance ($p < 0.05$); positive t values indicate that RMS errors decreased from the beginning to the end of the trials.

*FIG. 7*

TABLE 3. Comparison of stance duration symmetry and swing duration symmetry before and after tuning prosthesis controller.

| Method | Subject | | | |
|---|---|---|---|---|
| | AB1 | AB2 | TF1 | TF2 |
| Stance | | | | |
| HME | | | | |
| t | 4.69 | 4.97 | 3.01 | — |
| p | 0.001 | <0.001 | 0.01 | — |
| CES | | | | |
| t | 5.02 | 3.15 | 1.01 | 1.47 |
| p | <0.001 | 0.008 | 0.173 | 0.092 |
| Swing | | | | |
| HME | | | | |
| t | 3.20 | 4.95 | 2.39 | — |
| p | 0.008 | <0.001 | 0.024 | — |
| CES | | | | |
| t | 5.87 | 5.88 | 0.54 | 5.10 |
| p | <0.001 | <0.001 | 0.304 | <0.001 |

Statistical comparisons were made within each subject across trials (DF = 7). Bold characters indicate statistical significance ($p < 0.05$); positive $t$ values indicate smaller absolute values of symmetry indices (improved gait symmetry) after tuning.

FIG. 9

TABLE 4. Comparison of step width before and after tuning prosthesis controller.

| Method | Subject | | | |
|---|---|---|---|---|
| | AB1 | AB2 | TF1 | TF2 |
| HME | | | | |
| $t$ | 4.84 | 2.55 | 6.90 | — |
| $p$ | <0.001 | 0.019 | <0.001 | — |
| CES | | | | |
| $t$ | 3.67 | 1.04 | 0.56 | 2.59 |
| $p$ | 0.004 | 0.166 | 0.298 | 0.018 |

Statistical comparisons were made within each subject across trials (DF = 7). Bold characters indicate statistical significance ($p < 0.05$); positive $t$ values indicate that step width was smaller after tuning.

*FIG. 11*

SYSTEMS AND METHODS FOR AUTOMATICALLY TUNING POWERED PROSTHESIS IMPEDANCE CONTROL PARAMETERS

CROSS-REFERENCE TO RELATED APPLICATIONS

This application claims the benefit of U.S. Provisional Patent Application No. 62/247,553, filed on Oct. 28, 2015, entitled "SYSTEMS AND METHODS FOR AUTOMATICALLY TUNING POWERED PROSTHESIS IMPEDANCE CONTROL PARAMETERS," the disclosure of which is expressly incorporated herein by reference in its entirety.

BACKGROUND

Over 600,000 people in the US live with major lower limb loss, and the prevalence of limb amputation is expected to double by 2050. Many amputees rely on lower limb prostheses to regain some function of the missing limb, though their mobility, stability, and community participation remain substantially limited. Compared to traditional energetically-passive devices, modern powered knee prostheses promise to restore more natural locomotion and provide greater functionality. Most powered knee prostheses rely on finite state impedance control (IC), which adjusts the impedance of the knee joints based on gait phase. The desired IC parameter values in each gait phase are often fine-tuned manually and heuristically by a prosthetist, based on observations of the patient's gait performance and feedback, until the amputee's gait "looks good". In other words, the IC parameters are manually fine-tuned based on qualitative observations of the subject according to conventional techniques. Manual tuning presents a serious clinical challenge since it lacks precision, is time and resource intensive, and must be conducted uniquely for each amputee to account for between-patient variation. New approaches that can configure the prosthesis control parameters quickly and cost-effectively are needed to make powered lower limb prostheses more practical for clinical use.

The two main concepts to simplify the tuning procedure have been 1) to mimic able-bodied or sound limb impedance at prosthetic joints, and 2) to reduce the number of parameters that need to be tuned. Biological joint impedances have been computed directly from experimental measurements and estimated using biomechanical models. Due to experimental limitations, in vivo joint impedance during ambulation has only been measured at the ankle during the stance portion of gait. Impedance measurements at other joints, such as the knee, were made under static or quasi-static conditions and therefore may not transfer to dynamic ambulation tasks. Impedance estimated from musculoskeletal biomechanical models has only been validated for the stance phase of gait. Given the limited availability of biological impedance data, applying it toward the control of prosthetic joints during ambulation has not yet been demonstrated.

In a finite state machine-based controller, reducing the number of control parameters that must be calibrated may be achieved by defining fewer states. However, only modest simplification can be achieved since at least 3 states are typically defined for level-ground walking, and parameter values differ across tasks (e.g. ramp ascent/descent, stair ascent/descent). Another solution to tune fewer parameters is to associate parameter values with one another or with other intrinsic biomechanical measures (e.g. prosthesis joint angles, prosthesis load, walking speed, foot center of pressure, effective leg shape). In one case, this strategy not only reduced the burden of manual tuning, but also permitted alternate nonlinear control systems that had fewer control parameters altogether. However, given their complexity, explicit relationships between biomechanical measures and control parameters may be imprecisely known and potentially unsuitable as a basis for prosthesis control. Ultimately, parameter reduction only simplifies the tuning procedure, leaving many of the practical costs and challenges of tuning powered prostheses unsolved.

SUMMARY

An example system for tuning powered prosthesis impedance control parameters can include a powered prosthesis and intelligent tuner operably connected to the powered prosthesis. The intelligent tuner can be configured to adjust one or more of a plurality of impedance control parameters using a rule base. In addition, the powered prosthesis can include a joint, a motor that is mechanically coupled to the joint, a plurality of sensors configured to measure a plurality of gait parameters associated with a subject, and an impedance controller. The motor of the powered prosthesis can be configured to drive the joint, and the impedance controller of the powered prosthesis can be configured to output a control signal for adjusting a torque of the motor, where the torque is adjusted as a function of the measured gait parameters and the impedance control parameters.

Additionally, the intelligent tuner can be configured to adjust one or more of the impedance control parameters to achieve a target gait characteristic. Optionally, the target gait characteristic can be a gait characteristic of a non-disabled subject, for example.

Alternatively or additionally, the rule base can include a plurality of rules that link changes in the measured gait parameters to corresponding adjustments to the impedance control parameters. Optionally, changes in the measured gait parameters can be a respective difference between each of the measured gait parameters and a respective target gait parameter. Optionally, the rule base can include a respective set of rules for each of the impedance control parameters. Alternatively or additionally, the rule base can optionally include a respective set of rules for each of a plurality of gait cycle states. Additionally, the intelligent tuner can optionally be configured to adjust the impedance control parameters associated with each of the gait cycle states.

Alternatively or additionally, the powered prosthesis can optionally include a finite state machine configured to determine a gait cycle state based on the measured gait parameters. Optionally, the gait cycle states can be a plurality of level ground walking gait cycle states.

Alternatively or additionally, the powered prosthesis can optionally include a computing device configured to receive the measured gait parameters and determine one or more gait events.

Alternatively or additionally, the intelligent tuner can optionally be a fuzzy logic tuner.

Alternatively or additionally, the measured gait parameters can optionally include a joint angle, a joint angular velocity, a duration of a gait cycle state, or a load applied to the joint.

Alternatively or additionally, the impedance control parameters can optionally include a stiffness, an equilibrium position, or a damping coefficient.

Alternatively or additionally, the joint can optionally be a prosthetic knee joint, a prosthetic ankle joint, or a prosthetic hip joint.

An example computer-implemented method for tuning powered prosthesis impedance control parameters can include receiving a plurality of gait parameters associated with a subject, adjusting at least one impedance control parameter of a powered prosthesis using a rule base, and transmitting the at least one impedance control parameter to the powered prosthesis. The rule base can include a plurality of rules that link changes in the gait parameters to corresponding adjustments to a plurality of impedance control parameters.

Additionally, the computer-implemented method can further include adjusting one or more of the plurality of impedance control parameters to achieve a target gait characteristic. Optionally, the target gait characteristic can be a gait characteristic of a non-disabled subject, for example.

Alternatively or additionally, changes in the gait parameters can optionally be a respective difference between each of the gait parameters and a respective target gait parameter. Optionally, the rule base can include a respective set of rules for each of the impedance control parameters. Alternatively or additionally, the rule base can optionally include a respective set of rules for each of a plurality of gait cycle states. Optionally, the computer-implemented method can further include adjusting the impedance control parameter associated with each of the gait cycle states.

Additionally, the computer-implemented method can further include receiving a gait cycle state associated with the subject. Optionally, the gait cycle states can be a plurality of level ground walking gait cycle states.

Alternatively or additionally, the impedance control parameter can optionally be adjusted using fuzzy logic.

Alternatively or additionally, the measured gait parameters can optionally include a joint angle, a joint angular velocity, a duration of a gait cycle state, a load applied to the joint, or a trunk orientation.

Alternatively or additionally, the impedance control parameters can optionally include a stiffness, an equilibrium position, or a damping coefficient.

It should be understood that the above-described subject matter may also be implemented as a computer-controlled apparatus, a computer process, a computing system, or an article of manufacture, such as a computer-readable storage medium.

BRIEF DESCRIPTION OF THE DRAWINGS

The components in the drawings are not necessarily to scale relative to each other. Like reference numerals designate corresponding parts throughout the several views.

FIG. 5 illustrates the initial impedance control parameter extreme values (Table 1).

FIG. 6A illustrates fuzzy rules used in the initial double stance phase (Table A). FIG. 6B illustrates fuzzy rules used in the single stance phase (Table B). FIG. 6C illustrates fuzzy rules used in the swing extension phase (Table C).

FIG. 7 illustrates the comparison of RMS errors at the beginning and end of trials (Table 2).

FIG. 9 illustrates the comparison of stance duration symmetry and swing duration symmetry before and after tuning the prosthesis controller (e.g., the impedance controller) (Table 3).

FIG. 11 illustrates the comparison of step width before and after tuning the prosthesis controller (e.g., the impedance controller) (Table 4).

DETAILED DESCRIPTION

Unless defined otherwise, all technical and scientific terms used herein have the same meaning as commonly understood by one of ordinary skill in the art. Methods and materials similar or equivalent to those described herein can be used in the practice or testing of the present disclosure. As used in the specification, and in the appended claims, the singular forms "a," "an," "the" include plural referents unless the context clearly dictates otherwise. The term "comprising" and variations thereof as used herein is used synonymously with the term "including" and variations thereof and are open, non-limiting terms. The terms "optional" or "optionally" used herein mean that the subsequently described feature, event or circumstance may or may not occur, and that the description includes instances where said feature, event or circumstance occurs and instances where it does not. While implementations will be described for tuning impedance control parameters for a powered knee prosthesis, it will become evident to those skilled in the art that the implementations are not limited thereto, but are applicable for tuning impedance control parameters for any powered prosthesis, exoskeleton, or limb rehabilitation robot.

Systems and methods for automatically tuning the impedance control parameters for powered prostheses using a cyber expert system (CES) are described herein. A branch of artificial intelligence, CESs encode human expert (HME) factual knowledge and skills into a computer system as databases and rules. HME knowledge and skills can be represented in several ways, including a semantic network, production rules, predicate logic, object-attribute-value, hybrids, and scripts, depending on the type of knowledge and field of application. In an example described below, HMEs tuned prosthesis control parameters by qualitatively observing knee kinematics and gait characteristics (e.g. stride length and step symmetry). In other words, HMEs tuned the impedance control parameters based on qualitative observations of the subject using the powered prosthesis. On the other hand, using the systems and methods described herein, the impedance control parameters are automatically tuned based on quantitative measures of the gait characteristics of the subject using the powered prosthesis. The gait characteristics can be measured using sensors embedded in the powered prosthesis and can be communicated to an intelligent tuner, which adjusts the impedance control parameters to achieve a target gait characteristic (e.g., non-disabled walking). The systems and methods described herein can encode the HME knowledge and skills into a computer system by linking the measured gait parameters to corresponding adjustments to the impedance control parameters. Additionally, since tuning decisions vary depending on the magnitude of observed, continuously varying gait characteristics, HME knowledge can be represented in a sliding scale manner using fuzzy logic.

Figure 1A:
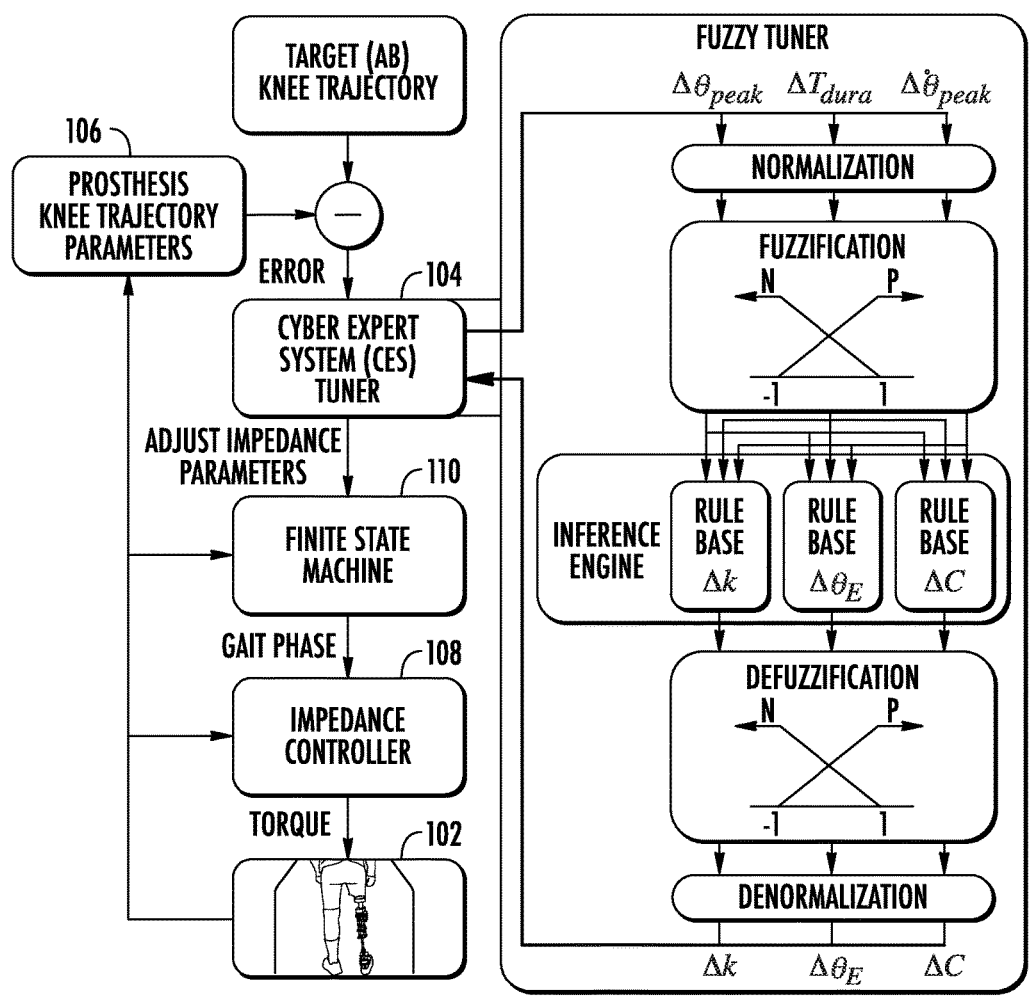
FIG. 1A is a block diagram of a system for tuning powered prosthesis impedance control parameters.
Figure 1B:
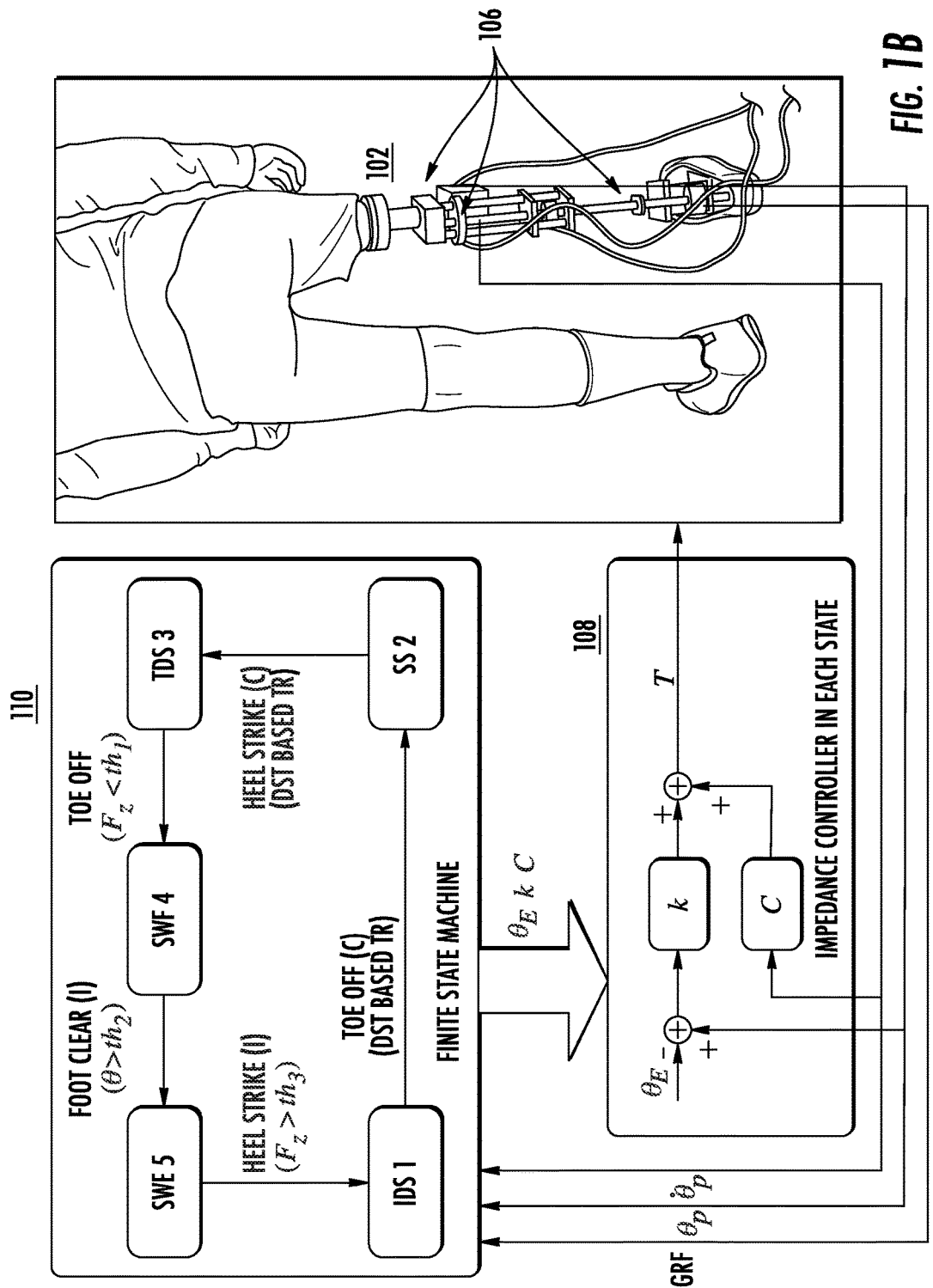
FIG. 1B is a block diagram of an example powered prosthesis.

Referring now to FIGS. 1A-1B, a system for tuning powered prosthesis impedance control parameters is described. The system can include a powered prosthesis and an intelligent tuner 104 operably connected to the powered prosthesis. The powered prosthesis and the intelligent tuner can be operably connected by any suitable communication link. For example, a communication link may be implemented by any medium that facilitates data exchange including, but not limited to, wired, wireless and optical links. Optionally, the powered prosthesis can be a powered knee prosthesis (PKP). An example PKP 102 is shown in FIGS. 1A and 1B. Although examples are provided where the powered prosthesis is a PKP herein, it should be understood that that the techniques described herein can be used for tuning impedance control parameters for other powered prosthesis devices. For example, the techniques described herein can be used for tuning impedance control parameters for a prosthetic leg, which can include one or more prosthetic joints (e.g., prosthetic hip, knee, and/or ankle joints). Additionally, a prosthetic leg can include combinations of prosthetic joints. Additionally, a bilateral amputee uses two prosthetic legs, where each prosthetic leg can include one or more prosthetic joints. This disclosure contemplates that the techniques described herein can be used for tuning the impedance control parameters for one or more of the prosthetic joints in a prosthetic leg. In addition, this disclosure contemplates that the techniques described herein can be used for tuning the impedance control parameters for passive prosthetic leg, exoskeletons and/or limb rehabilitation robots.

The powered prosthesis can include a joint and a motor that is mechanically coupled to the joint. The motor can be configured to drive the joint. For example, an example PKP can include a prosthetic knee joint having a moment arm and pylon that is driven by a direct current motor (Maxon, Switzerland) through a ball screw (THK, Japan). The powered prosthesis can also include a plurality of sensors 106 configured to measure a plurality of gait parameters associated with a subject. The gait parameters can optionally include a joint angle, a joint angular velocity, a duration of a gait cycle state, or a load applied to the joint. For example, the sensors 106 can include a sensor for measuring joint angle (e.g., a potentiometer), a sensor for measuring joint angular velocity (e.g., an encoder operably connected to the motor), and a sensor for measuring ground reaction force (GRF) (e.g., a load sensor such as a 6 degree of freedom load cell). The sensors 106 can be embedded in the powered prosthesis as shown in FIG. 1B. In addition, the gait parameters can be sampled using a multi-functional data acquisition card (National Instruments, TX, USA). The gait parameters can then be communicated to a finite state machine, an impedance controller, an intelligent tuner, etc. as described herein. This disclosure contemplates that the powered prosthesis, finite state machine, impedance controller, intelligent tuner, etc. can be operably connected by any suitable communication link. For example, a communication link may be implemented by any medium that facilitates data exchange including, but not limited to, wired, wireless and optical links. It should be understood that the gait parameters and sensors described above are provided only as examples. This disclosure contemplates that other gait parameters can be measured including, but not limited to, angular acceleration, angular jerk, foot orientation, shank orientation, thigh orientation, trunk orientation (trunk motion arc), lower limb segment orientation, hip height, knee height, ankle height, location of foot center of pressure, speed of foot center of pressure, acceleration of foot center of pressure, location of center of mass, velocity of center of mass, and/or acceleration of center of mass. In addition, these gait parameters can be measured using one or more of the following sensors: a foot switch, an accelerometer, an inertial moment unit, a foot pressure sensor, a strain gauge, force plate, and/or a motion capture system (e.g., an imaging system).

The powered prosthesis can also include an impedance controller 108 that is configured to output a control signal for adjusting a torque of the motor. The impedance controller 108 can be operably connected to the motor of the powered prosthesis using any suitable communication link that facilitates data exchange. For example, the impedance controller 108 can adjust the torque as a function of the measured gait parameters and a plurality of impedance control parameters as shown by:

$$\tau = k(\theta_P - \theta_E) + C\dot{\theta}_P,$$

where joint angle ($\theta_P$) and angular velocity ($\dot{\theta}_P$) are the measured gait parameters (e.g., measured using the sensors described above) and stiffness (k), equilibrium position ($\theta_E$), and damping coefficient (C) are the impedance control parameters. This is also shown in FIG. 1B, where the measured gait parameters (joint angle ($\theta_P$) and angular velocity ($\dot{\theta}_P$)) are received by the impedance controller 108, which then adjust the torque ($\tau$) as a function of the measured gait parameters and the impedance control parameters (stiffness (k), equilibrium position ($\theta_E$), and damping coefficient (C)) by outputting a control signal for controlling the motor of the powered prosthesis. It should be understood that stiffness (k), equilibrium position ($\theta_E$), and damping coefficient (C) are provided only as example impedance control parameters. This disclosure contemplates using any impedance control parameters in the techniques described herein including, but not limited to, linear or nonlinear stiffness, equilibrium position, and/or linear or nonlinear damping coefficients. As described herein, each of the impedance control parameters (e.g., stiffness) can have a respective value for each of a plurality of gait cycle states of the powered prosthesis. As described below, a finite machine can be used to detect a plurality of gait cycle states. The gait cycle states of the powered prosthesis can be the same gait cycle states defined by clinicians to describe gait cycle for abled-body subjects during level ground walking, for example. The level ground walking gait cycle can be divided into a plurality of gait cycle states (or phases)—initial double support (IDS), single support (SS), terminal double support (TDS), swing flexion (SWF), and swing extension (SWE). Accordingly, the stiffness impedance control parameter can have a respective value for each of a plurality of gait cycle states. It should be understood that gait cycles are not limited to level ground walking and can include, but are not limited to, other walking cycles such as ramp ascent/descent and stair ascent/descent.

The powered prosthesis can optionally include a finite state machine 110 configured to determine the gait cycle state based on the measured gait parameters. This is also shown in FIG. 1B, where the measured gait parameters (joint angle ($\theta_p$), joint angular velocity ($\dot{\theta}_p$), and ground reaction force (GRF)) are received by the finite state machine 110. Gait cycle states can be defined based on the expected values of the gait parameters (such as joint angle, joint angular velocity, and GRF) in the respective gait cycle states. For example, the gait cycle states can be the level ground walking gait cycle states (or phases) described above. Thus, the finite state machine 110 can be configured to detect transitions between the gait cycle states by monitoring the measured gait parameters and comparing the measured gait parameters to the gait cycle state definitions. Additionally, each of the impedance control parameters can have a respective value in a plurality of gait cycle states. For example, each of stiffness (k), equilibrium position ($\theta_E$), and damping coefficient (C) can have a respective value for each of gait cycle states IDS, SS, TDS, SWF, and SWE. Alternatively or additionally, the powered prosthesis can optionally include a computing device configured to detect one or more gait events including, but not limited to, heel strike, toe off, and/or foot flat. For example, a gait event can be defined based on the expected values of the gait parameters such as joint angle, joint angular velocity, GRF, and foot pressure distribution during the gait event. Thus, the computing device can be configured to detect a gait event by monitoring the measured gait parameters and comparing the measured gait parameters to the gait event definition. Optionally, in some implementations, the finite state machine 110 can use information regarding gait events to determine the gait cycle state.

As described above, the system can include an intelligent tuner 104 operably connected to the powered prosthesis. The intelligent tuner 104 can be configured to adjust one or more of the impedance control parameters to achieve a target gait characteristic (e.g., a gait characteristic of a non-disabled subject). The intelligent tuner 104 can be configured to implement intelligent computing techniques including, but not limited to, fuzzy logic, neural networks, physical models, reinforcement learning based systems, knowledge-based systems, case-based reasoning, semantic network, predicate logic, object-attribute-value, hybrids, and scripts, etc. in order to adjust the impedance control parameters to achieve the target gait characteristic. As shown in FIGS. 1A and 1B, the adjusted impedance control parameters can be provided to the impedance controller 108, which then adjust the torque ($\tau$) as a function of the measured gait parameters and the impedance control parameters by outputting a control signal for controlling the motor of the powered prosthesis.

For example, the intelligent tuner 104 can be configured to adjust one or more of a plurality of impedance control parameters using a rule base. Optionally, the intelligent tuner 104 can be a fuzzy logic tuner. The intelligent tuner 104 can encode human expert (HME) decision making into a computer system as databases and rules. As described above, HMEs conventionally tune prosthesis control parameters by qualitative observation of knee kinematics and gait characteristics (e.g. stride length and step symmetry) and adjusting the impedance control parameters based on the qualitative observations. In the system described herein, the sensors 106 of the powered prosthesis quantitatively measure a plurality of gait parameters associated with a subject such as a joint angle, a joint angular velocity, a duration of a gait cycle state, or a load applied to the joint. The rule base encodes the HME decision making by including a plurality of rules that link changes in the measured gait parameters to corresponding adjustments to the impedance control parameters. Optionally, changes in the measured gait parameters can be a respective difference between each of the measured gait parameters and a respective target gait parameter. Optionally, the rule base can include a respective set of rules for each of the impedance control parameters. Alternatively or additionally, the rule base can optionally include a respective set of rules for each of a plurality of gait cycle states. Thus, it is possible to track the normative knee trajectory more precisely by tuning based on quantitative measures as compared to HME tuning by qualitative observation.

It should be appreciated that the logical operations described herein with respect to the various figures may be implemented (1) as a sequence of computer implemented acts or program modules (i.e., software) running on a computing device (e.g., the computing device described in FIG. 2), (2) as interconnected machine logic circuits or circuit modules (i.e., hardware) within the computing device and/or (3) a combination of software and hardware of the computing device. Thus, the logical operations discussed herein are not limited to any specific combination of hardware and software. The implementation is a matter of choice dependent on the performance and other requirements of the computing device. Accordingly, the logical operations described herein are referred to variously as operations, structural devices, acts, or modules. These operations, structural devices, acts and modules may be implemented in software, in firmware, in special purpose digital logic, and any combination thereof. It should also be appreciated that more or fewer operations may be performed than shown in the figures and described herein. These operations may also be performed in a different order than those described herein.

Figure 2:
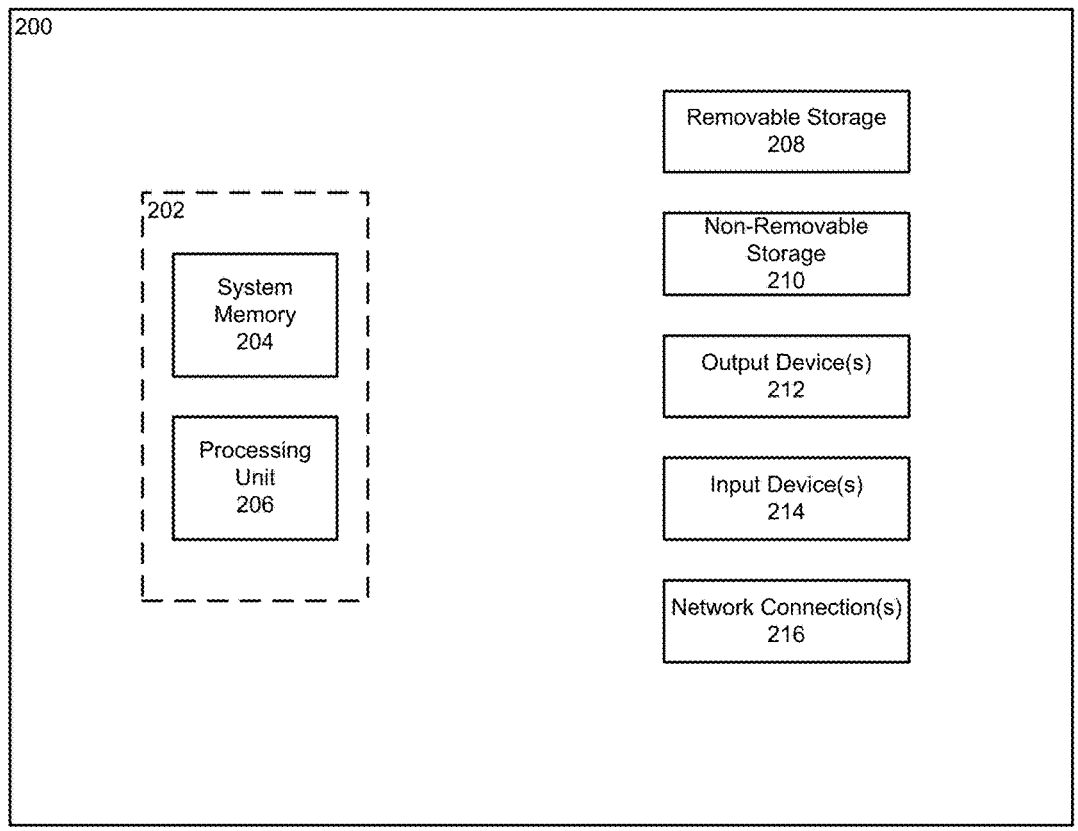
FIG. 2 is an example computing device.

Referring to FIG. 2, an example computing device 200 upon which embodiments of the invention may be implemented is illustrated. This disclosure contemplates that the impedance controller, the finite state machine, and/or the intelligent tuner can be implemented using a computing device such as computing device 200. It should be understood that the example computing device 200 is only one example of a suitable computing environment upon which embodiments of the invention may be implemented. Optionally, the computing device 200 can be a well-known computing system including, but not limited to, personal computers, servers, handheld or laptop devices, multiprocessor systems, microprocessor-based systems, network personal computers (PCs), minicomputers, mainframe computers, embedded systems, and/or distributed computing environments including a plurality of any of the above systems or devices. Distributed computing environments enable remote computing devices, which are connected to a communication network or other data transmission medium, to perform various tasks. In the distributed computing environment, the program modules, applications, and other data may be stored on local and/or remote computer storage media.

In its most basic configuration, computing device 200 typically includes at least one processing unit 206 and system memory 204. Depending on the exact configuration and type of computing device, system memory 204 may be volatile (such as random access memory (RAM)), non-volatile (such as read-only memory (ROM), flash memory, etc.), or some combination of the two. This most basic configuration is illustrated in FIG. 2 by dashed line 202. The processing unit 206 may be a standard programmable processor that performs arithmetic and logic operations necessary for operation of the computing device 200. The computing device 200 may also include a bus or other communication mechanism for communicating information among various components of the computing device 200.

Computing device 200 may have additional features/functionality. For example, computing device 200 may include additional storage such as removable storage 208 and non-removable storage 210 including, but not limited to, magnetic or optical disks or tapes. Computing device 200 may also contain network connection(s) 216 that allow the device to communicate with other devices. Computing device 200 may also have input device(s) 214 such as a keyboard, mouse, touch screen, etc. Output device(s) 212 such as a display, speakers, printer, etc. may also be included. The additional devices may be connected to the bus in order to facilitate communication of data among the components of the computing device 200. All these devices are well known in the art and need not be discussed at length here.

The processing unit 206 may be configured to execute program code encoded in tangible, computer-readable media. Tangible, computer-readable media refers to any media that is capable of providing data that causes the computing device 200 (i.e., a machine) to operate in a particular fashion. Various computer-readable media may be utilized to provide instructions to the processing unit 206 for execution. Example tangible, computer-readable media may include, but is not limited to, volatile media, non-volatile media, removable media and non-removable media implemented in any method or technology for storage of information such as computer readable instructions, data structures, program modules or other data. System memory 204, removable storage 208, and non-removable storage 210 are all examples of tangible, computer storage media. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 206 may execute program code stored in the system memory 204. For example, the bus may carry data to the system memory 204, from which the processing unit 206 receives and executes instructions. The data received by the system memory 204 may optionally be stored on the removable storage 208 or the non-removable storage 210 before or after execution by the processing unit 206.

It should be understood that the various techniques described herein may be implemented in connection with hardware or software or, where appropriate, with a combination thereof. Thus, the methods and apparatuses of the presently disclosed subject matter, or certain aspects or portions thereof, may take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs may implement or utilize the processes described in connection with the presently disclosed subject matter, e.g., through the use of an application programming interface (API), reusable controls, or the like. Such programs may be implemented in a high level procedural or object-oriented programming language to communicate with a computer system. However, the program(s) can be implemented in assembly or machine language, if desired. In any case, the language may be a compiled or interpreted language and it may be combined with hardware implementations.

Figure 3:
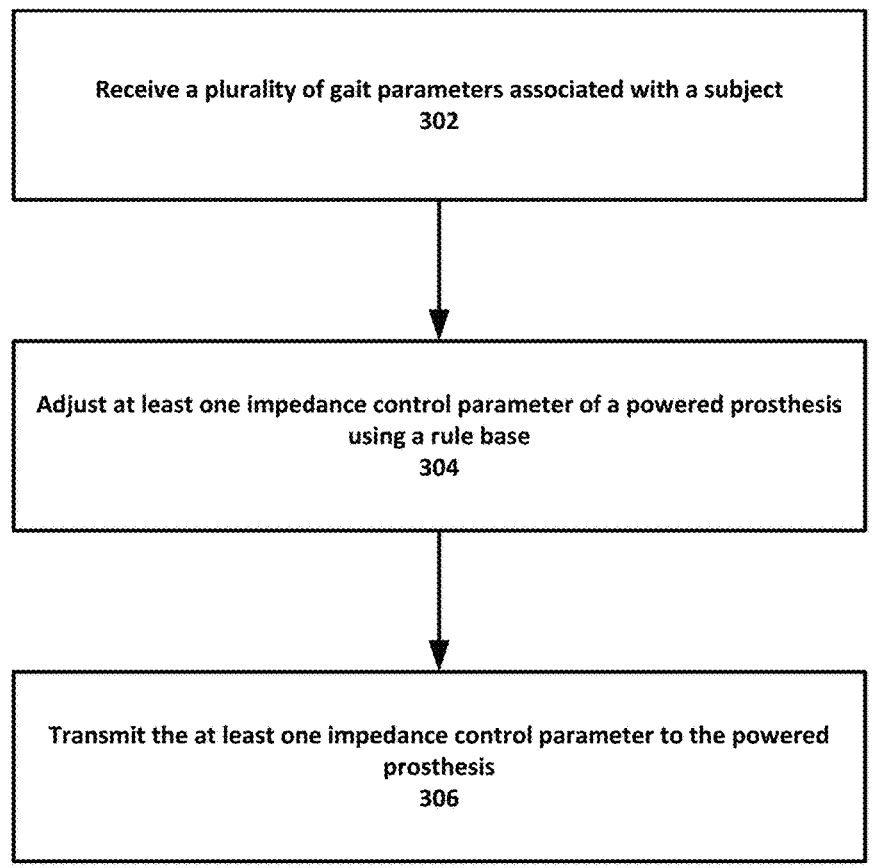
FIG. 3 is a flow diagram of example operations for tuning powered prosthesis impedance control parameters.

Referring now to FIG. 3, a flow diagram of example operations 300 for tuning powered prosthesis impedance control parameters is shown. In some implementations, the example operations 300 can be implemented by an intelligent tuner (e.g., the intelligent tuner 104 of FIG. 1A). At 302, a plurality of gait parameters associated with a subject are received. As described above, the gait parameters can optionally be measured by sensors embedded in a powered prosthesis (e.g., the sensors 106 of the powered prosthesis of FIGS. 1A-1B). Optionally, the gait parameters can include a joint angle, a joint angular velocity, a duration of a gait cycle state, a load applied to the joint, and/or a trunk orientation (trunk motion arc). At 304, at least one impedance control parameter of a powered prosthesis is adjusted using a rule base. Optionally, the impedance control parameters can include a stiffness, an equilibrium position, or a damping coefficient. At 306, the at least one impedance control parameter is transmitted to the powered prosthesis. For example, the impedance control parameter can be transmitted to an impedance controller (e.g., the impedance controller 108 of the powered prosthesis of FIGS. 1A and 1B). As described above, the rule base can include a plurality of rules that link changes in the gait parameters to corresponding adjustments to a plurality of impedance control parameters.

EXAMPLES

Materials and Methods
Prosthesis Design and Control Structure

An example system and method for automatically tuning a powered knee prosthesis (PKP) are described below. The knee joint, comprised of a moment arm and pylon, was driven by a direct current motor (Maxon, Switzerland) through a ball screw (THK, Japan). Sensors were embedded in the PKP to measure knee joint angle (potentiometer), knee joint angular velocity (encoder connected with the motor), and ground reaction force (GRF) (6 degrees of freedom load cell (ATI, NC, USA) mounted in line with the shank pylon). The powered prosthesis was tethered and controlled by a desktop PC. A multi-functional data acquisition card (National Instruments, TX, USA) collected all sensor measurements at 100 Hz and provided digital-to-analog control output to drive the DC motor through a motor controller (Maxon, Switzerland). A low profile prosthetic foot (1E57 Lo Rider, Otto Bock, Germany) was used in the prototype.

Finite-state impedance control (IC) was used to control knee forces generated by the PKP during gait. The level ground walking gait cycle was divided into five states (phases): initial double support (IDS), single support (SS), terminal double support (TDS), swing flexion (SWF), and swing extension (SWE). Transitions between states were triggered by the GRF, knee joint angle, and knee joint angular velocity measured from the prosthesis. Within each state, three IC parameters, stiffness (k), equilibrium position ($\theta_E$), and damping coefficient (C), were set at constant values to modulate joint torques generated by the PKP as a function of the measured knee joint angle ($\theta_p$) and angular velocity ($\dot{\theta}_p$) during gait (Eq. 1).

$$\tau = k(\theta_p - \theta_E) + C\dot{\theta}_p \qquad \text{Eq. 1}$$

Experimental Protocol

A) Participants and Materials

The experimental protocol was approved by an Institutional Review Board (IRB) and all subjects gave their informed consent to participate. Two male able-bodied subjects (AB1 and AB2; height/weight: 181 cm/90 kg and 183 cm/93 kg, respectively) and two male unilateral traumatic transfemoral amputees (TF1 and TF2; height/weight: 182 cm/84 kg and 183 cm/100 kg, respectively) participated in this study. Three subjects (AB1, AB2, and TF1) participated in HME tuning trials and CES tuning trials; data collected during HME tuning trials were used to build the CES rule base. Subject TF2, whose data was not used to build the CES rule base, only participated in the CES tuning trials to evaluate the generalizability of the CES across amputees.

During all experiment trials, subjects walked on an instrumented treadmill at a speed of 0.6 m s$^{-1}$ to ensure that subjects could maintain a consistent gait pattern. Force plates mounted on the treadmill recorded GRFs under both feet. Intrinsic PKP mechanical measurements (e.g., prosthetic knee angle, angular velocity, and GRFs) were sampled at 1000 Hz. Forty-one reflective markers were attached to the torso, pelvis, and both lower limbs, while an eight-camera motion analysis system (VICON, Oxford, UK) captured the marker positions, sampled at 100 Hz. Subjects wore a fall-arrest harness while walking to ensure their safety. All measurements were synchronized.

Figure 4:
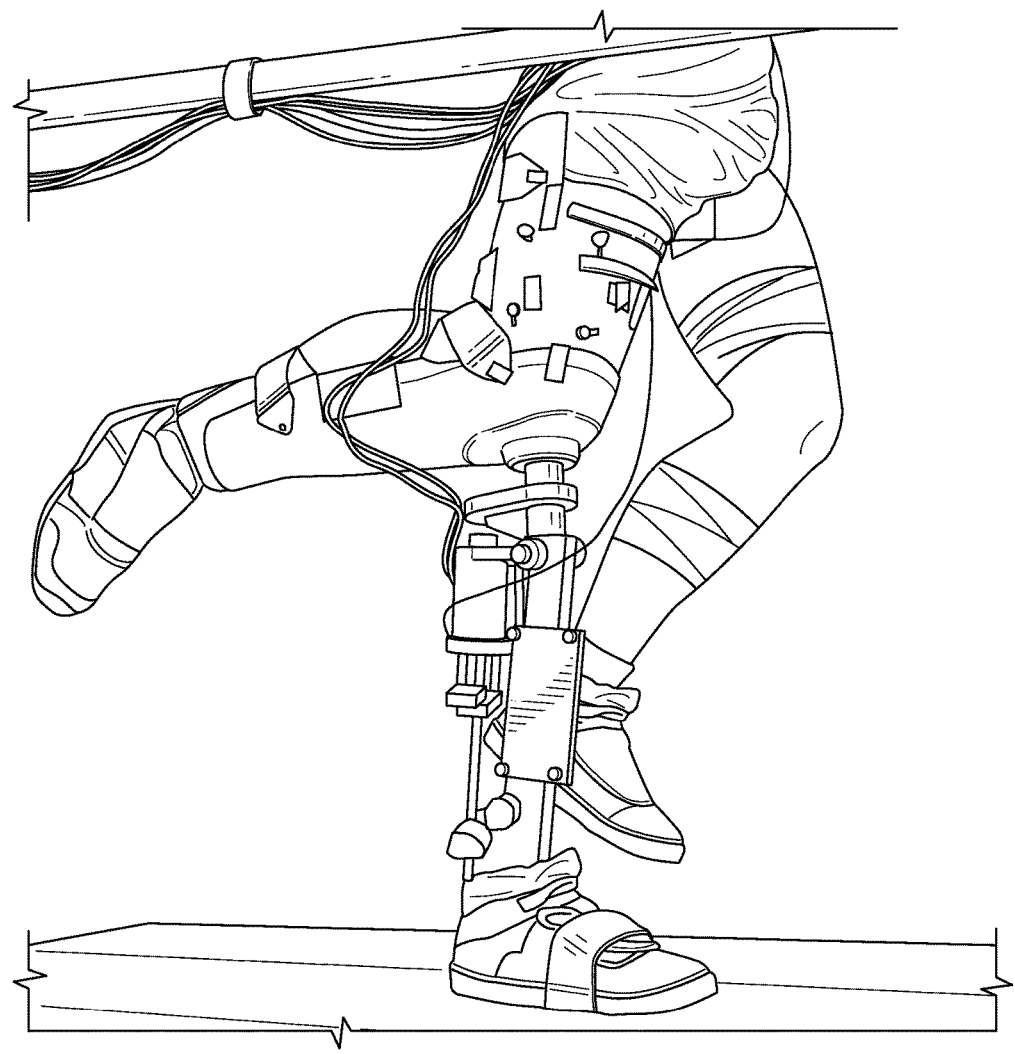
FIG. 4 illustrates a PKP prototype with an adapter allowing able-bodied subjects to walk with the prosthesis.

Before data collection, each subject was fit with the powered prosthesis. A special adaptor was made to allow able-bodied subjects to wear the powered prosthesis as shown in FIG. 4. On days prior to testing, subjects trained to walk with the PKP in the lab for approximately 10 hours until they felt comfortable walking at a speed of 0.6 m s$^{-1}$ without holding a railing.

B) Human Expert Tuning

In one condition, an experienced HME tuned the IC parameters of the PKP while subjects walked on a treadmill. The HME had designed the powered prosthesis and its control algorithm. Prior to this study, the HME had completed observational gait analysis and biomechanics courses, and independently conducted parameter tuning for twenty subjects.

Eight initial IC parameter sets in each gait phase were defined as one of 8 possible arrangements of the maximum and minimum values of each parameter (see Table 1 of FIG. 5) among fine-tuned parameters (unpublished data) of previous test subjects (14 able-bodied subjects and 6 transfemoral amputees). Eight IC parameter profiles containing initial IC parameter sets for all 5 gait phases were constructed. The order of sets within each phase was randomized using a random number generator algorithm in MATLAB (The MathWorks, Inc., Natick, Mass.).

Subjects AB1, AB2, and TF1 completed 8 walking trials during which the HME tuned IC parameters. The order in which the eight initial IC parameter profiles were used in each trial was randomized in MATLAB, again with a random number generator algorithm. Subjects were permitted to walk for approximately 10-20 strides before tuning began. The expert qualitatively observed subjects' gait performance (e.g. stride length, step symmetry, and trunk motion) and onboard sensor readings (i.e. PKP knee angle) from the prosthesis, and tuned IC parameters accordingly based on the qualitative observations. IC parameter values on the prosthesis were then updated based on the expert's tuning. The three procedures (observing, tuning, and updating) were conducted sequentially within each tuning cycle, which was repeated until the expert was satisfied with the prosthesis performance. In each tuning cycle, there was no limitation on how many IC parameters the expert could adjust. Subjects walked with fine-tuned IC parameters for 15 strides before the trial was stopped. To ensure that the expert tuned the parameters by observation rather than memory of previous tuning results, only incremental tuning was permitted; true IC values were not available to the expert during or after tuning.

C) Cyber Expert System Design

A CES based on fuzzy logic inference that encoded a human expert's knowledge and experience into computer rules to tune the IC parameters of a PKP was designed (see FIG. 1A). IC parameters were tuned to reproduce the average knee angle trajectory of healthy adults during level ground walking, since normative gait behavior has been the target of other powered knee prostheses. Three gait parameters, computed from intrinsic prosthesis measurements, were used to characterize the knee angle trajectory in each gait phase: peak knee angle ($\theta_{peak}$), gait phase duration ($T_{dura}$), and peak angular velocity ($\dot{\theta}_{peak}$). $\theta_{peak}$ was the maximum knee flexion angle for IDS, SWF, and the maximum knee extension angle for SS, SWE, and TDS. $\dot{\theta}_{peak}$ was the maximum flexion angular velocity for IDS, SS, SWF, and SWE and the maximum extension angular velocity for TDS.

For each gait phase (state), a fuzzy logic tuner was designed using the well-known WM approach from Wang and Mendel that has been widely used in other applications. This approach was chosen because it permits an adaptive, expandable rule base as more training data become available. Each fuzzy tuner consisted of a fuzzification block, rule-base, inference engine, and defuzzification block. During fuzzification, crisp inputs were converted into grades in individual membership functions that determined how inputs should be interpreted by the linguistic rules. The rule-base stored the knowledge, in the form of IF-THEN rules, of how to change outputs given a set of inputs. The inference engine determined which rule to use to map fuzzified inputs into fuzzified outputs. The defuzzification block converted the fuzzified output into crisp outputs.

The inputs of the fuzzy tuner for each gait phase were the difference ($\Delta\theta_{peak}$, $\Delta T_{dura}$, and $\Delta\dot{\theta}_{peak}$) between the prosthesis and target gait parameters averaged across five consecutive strides. The outputs were the changes in IC parameters ($\Delta k$, $\Delta\theta_E$, and $\Delta C$). Two trapezoid membership functions, negative (N) and positive (P), were defined for each input and output parameter, with the domain intervals of the fuzzy regions normalized by the minimum and maximum parameter values during the preliminary HME tuning experiments. Multiplication was used for the fuzzy "and" logic, while maximization was used for the "or" logic. The inference was made by clipping the output membership function at the input strength for each rule. The combination of outputs in multiple rules was achieved by fuzzy "or" logic. Crisp outputs were computed using a centroid defuzzification algorithm.

The CES was built with the fuzzy rule-base, which was established using data collected from the HME tuning trials for AB1, AB2, and TF1. For each instance when the HME adjusted the IC parameters, input-output data pairs having three inputs ($\Delta\theta_{peak}$, $\Delta T_{dura}$, and $\Delta\dot{\theta}_{peak}$) and one output ($\Delta k$, $\Delta\theta_E$, or $\Delta C$) were formulated and normalized by multiplying the maximum adjustment of that impedance parameter during HME tuning. Values in each input-output data pair were assigned to the membership function, either N or P, for which the projected function value, m, was higher. Rules in the form of IF-THEN statements were then generated for each data pair (e.g., Eq. 2).

Rule: IF $\Delta\theta_{peak}$ is N, $\Delta_{dura}$ is N, and $\Delta\dot{\theta}_{peak}$ is P,
    THEN $\Delta\theta_E$ is P.    Eq 2

To resolve conflicts between rules with the same IF part but different THEN parts, a degree D was assigned for each rule (Eq. 3), and only the rule with the highest degree in the conflict group was accepted for the final rule-base.

$$D(\text{Rule}) = m(\Delta\theta_{peak})m(\Delta T_{dura})m(\Delta\dot{\theta}_{peak})m(\Delta\theta_E) \quad \text{Eq. 3}$$

The final rule base (Table A, B, C of FIGS. 6A-6C) contained eight rules relating inputs to each output IC parameter, or 24 rules for each gait phase.

D) Cyber Expert Tuning

All four subjects participated in the CES tuning trials, conducted on different days from the previous procedures. Subjects AB1, AB2, and TF1 completed 16 walking trials (8 CES tuning, 8 non-tuning), while subject TF2 completed 8 walking trials with CES tuning only. The same eight initial IC parameter profiles and randomization procedure used in the HME tuning trials were adopted here in both the tuning and non-tuning trials. CES tuning was initiated approximately 30 seconds after starting the trial, and IC parameters were tuned only if specific criteria were met. To ensure that subjects had adjusted to current IC parameter values, the CES tuned impedance parameters if the variance in gait parameters ($\theta_{peak}$, $T_{dura}$, $\dot{\theta}_{peak}$) over five consecutive strides was less than the parameter variance during walking following HME tuning. During online tuning, gait parameter errors ($\Delta\theta_{peak}$, $\Delta T_{dura}$, and $\Delta\dot{\theta}_{peak}$) averaged over the last 5 consecutive strides were used as CES inputs. The impedance values were updated based on the CES outputs. The CES stopped tuning when the root-mean-square (RMS) error between the prosthesis and target knee joint angles over five consecutive strides was less than 3°, or 1.5 times the joint angle standard deviation during walking in healthy adults. Subjects walked with fine-tuned IC parameters for 15 strides before the trial was stopped.

Data Analysis to Compare HME and CES Tuning Performance

The RMS error between the prosthesis knee motion and target knee joint angle representing normative knee kinematics during walking was computed. Common global measures of gait performance was also computed as an indicator of subjects' overall adaptation to the prosthesis over a trial, including stance/swing duration index, step width, and trunk sway.

Stance and swing duration symmetry, common measures of general gait performance in lower limb amputees, were quantified by the symmetry index (Eq. 4), where S and P are the gait phase duration of subjects' sound and prosthetic lower limbs, respectively.

$$SI = \frac{(S-P)}{(S+P)\times 0.5} \quad \text{Eq. 4}$$

Step width, an indicator of stability, was computed as the medial-lateral distance between heel markers at heel strike. Trunk sway, another indicator of stability, was computed as the peak-to-peak distance of the T10 spinal vertebra (located with a reflective marker by motion capture) in the lateral-medial and anterior-posterior directions during a stride cycle. Trunk movement was monitored only for subjects TF1 and TF2.

As the tuning procedure progressed, symmetry index magnitude was expected to decrease if bilateral gait timing became more symmetric; step width was expected to decrease if subjects felt more stable; and trunk movement was expected to decrease if subjects' balance improved.

RMS error, symmetry index, step width, and trunk sway were computed for each stride and averaged over 10 consecutive strides at both the beginning and end of trials. For both CES and HME tuning methods, these quantified metrics were compared before and after tuning IC parameters; a one-tailed paired Student's t-test was conducted across trials within each individual subject. Additionally, the quantified metrics derived after HME tuning were compared to those derived after CES tuning using two-tailed paired Student's t-tests across subjects AB1, AB2, and TF1.

As a measure of the repeatability of CES and HME tuning, the coefficient of variation (CV), the ratio of the standard deviation to the mean, in fine-tuned IC parameters was computed for each subject and each gait phase. The CV across phases for each subject was averaged and then compared the CV between HME and CES using two-tailed paired Student's t-tests across AB1, AB2, and TF1.

For all statistical comparisons, significant differences were defined for $p<0.05$.

Results

Figure 8:
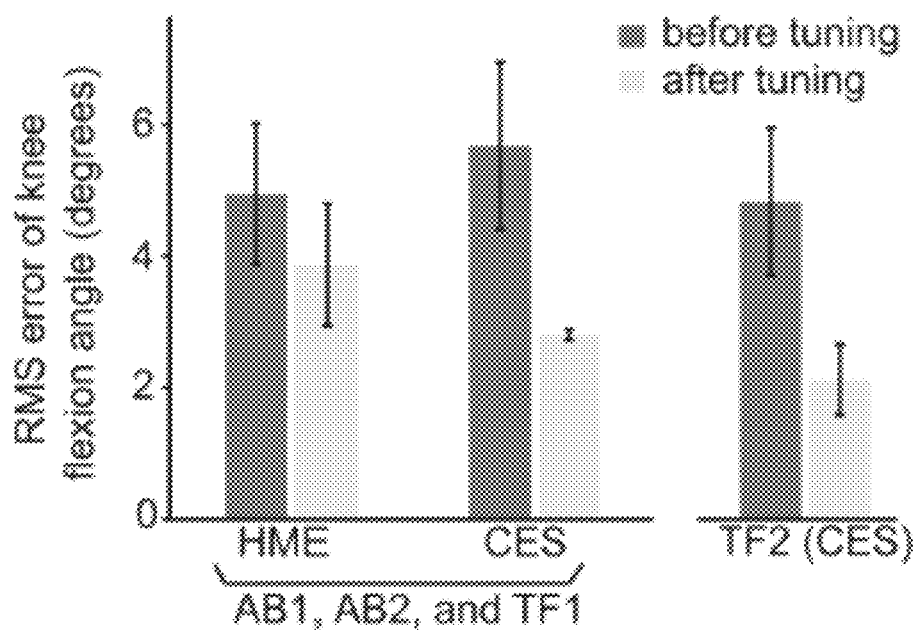
FIG. 8 illustrates mean (+/−SD) RMS error between prosthetic knee and target knee angle trajectories before and after tuning. For HME and CES tuning, RMS errors were averaged across trials first; the showed mean (+/−SD) was averaged across three subjects. TF2's data, which were not used to build CES, was averaged over eight CES tuning trials.

Both CES and HME tuning produced a more normative prosthetic knee angle trajectory. For both tuning methods, post-tuning RMS error decreased significantly compared to pre-tuning RMS errors in AB1, AB2, and TF1 (see statistics in Table 2 of FIG. 7). This was also observed in the CES tuning trials collected from TF2, whose data were not used to build the CES rule base (Table 2 and FIG. 8). For non-tuning trials within each subject, a slight, but non-significant, reduction of RMS errors was observed at the end of the trials (Table 2), indicating that improvement in knee angle trajectory over the tuning trials was primarily due to tuning rather than to subjects' adaptation to initial IC parameters. CES tuning yielded smaller RMS errors than HME tuning, consistently observed in AB1, AB2, and TF1. Compared to RMS errors after HME tuning averaged across subjects, RMS errors after CES tuning (FIG. 8) showed more consistent and lower values. However, the post-tuning RMS error difference between CES and HME tuning trials was not statistically significant across 3 tested subjects (p=0.210, t=1.82, DF=2) (FIG. 8).

Figure 10:
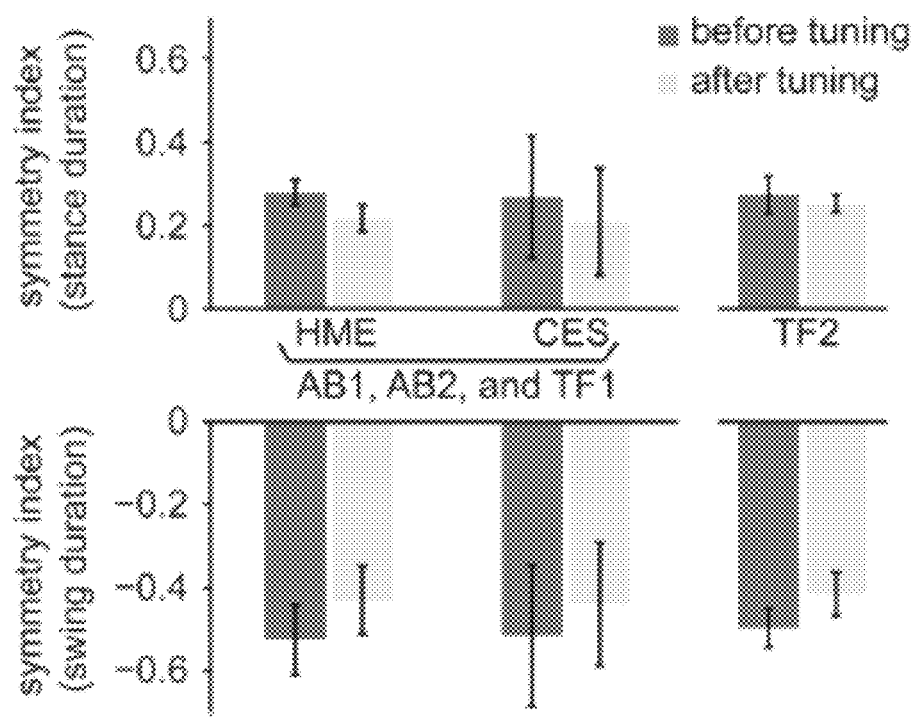
FIG. 10 illustrates (top portion of FIG. 10) mean (+/−SD) stance duration and (bottom portion of FIG. 10) swing duration symmetry index before and after tuning. For HME and CES tuning, symmetry indices were averaged across trials first; the showed mean (+/−SD) was averaged across three subjects. TF2's data, which were not used to build CES, was averaged over eight CES tuning trials.

Stance and swing duration symmetry improved significantly after HME tuning for subjects AB1, AB2, and TF1 (Table 3 of FIG. 9). The gait symmetry of each tested subject also improved after CES tuning, but not all improvements were statistically significant (Table 3). There was no difference in the subjects' post-tuning stance (p=0.916, t=0.12, DF=2) or swing (p=0.868, t=0.19, DF=2) duration symmetry between HMS and CES tuning trials (FIG. 10).

Figure 12:
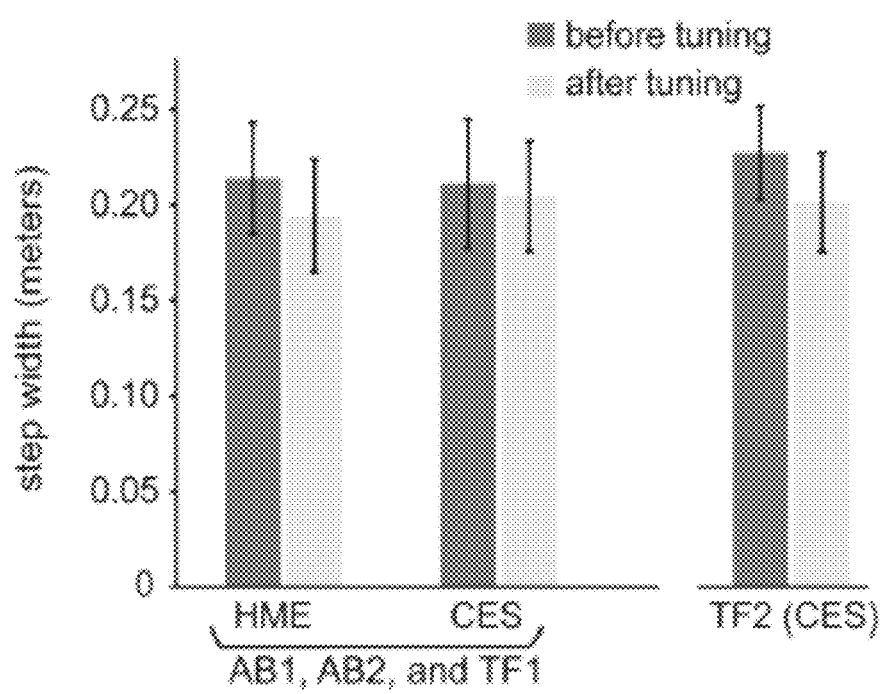
FIG. 12 illustrates mean (+/−SD) step width before and after tuning. For HME and CES tuning, step width was averaged across trials first; the showed mean (+/−SD) was averaged across three subjects. TF2's data, which were not used to build CES, was averaged over eight CES tuning trials.

Both HME tuning and CES tuning reduced the step width of each subject (Table 4 of FIG. 11 and FIG. 12). The step width reductions were statistically significant for all subjects who participated in HME tuning, while reductions from CES tuning were significant only for subjects AB1 and TF2 (Table 4). Compared with HME, CES yielded comparable post-tuning step width averaged across 3 subjects (p=0.518, t=0.78, DF=2) (FIG. 12).

Figure 13:
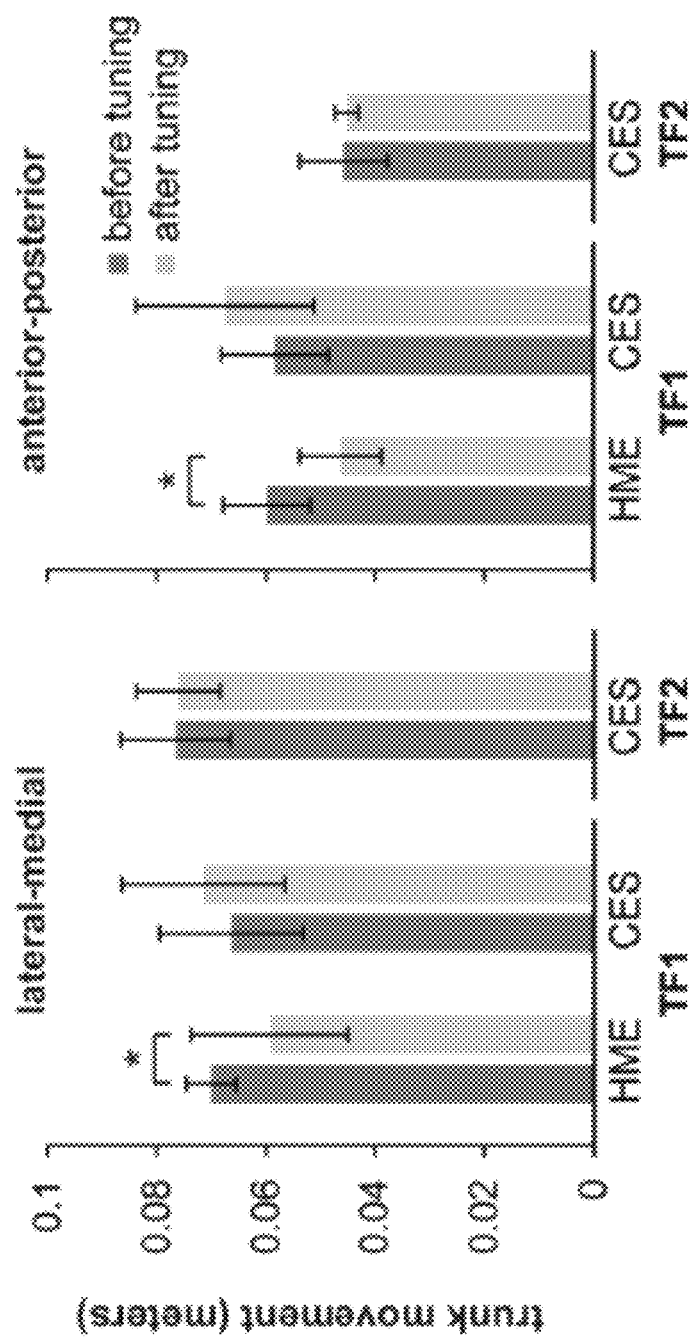
FIG. 13 illustrates mean (+/−SD) trunk sway before and after tuning. Trunk sway was only measured for subjects TF1 and TF2. TF2 only participated in CES tuning procedure. Hence, the results were averaged across eight trials of each tuning method for each subject. * denotes statistical significance ($p<0.05$).

The trunk sway was captured from TF1 during HME and CES tuning, and from TF2 during CES tuning only. For TF1, HME tuning significantly reduced trunk sway in the lateral-medial (p=0.022, t=2.45, DF=7) and anterior-posterior (p=0.007, t=3.28, DF=7) directions, while CES tuning yielded slightly higher trunk sway in both directions (FIG. 13). For TF2, CES tuning did not change trunk sway (FIG. 13).

Figure 14:
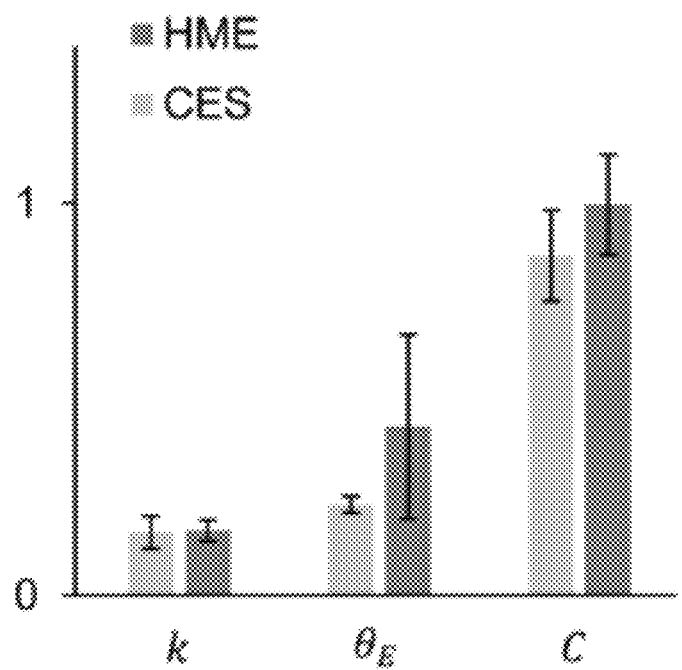
FIG. 14 illustrates mean (+/−SD) coefficient of variation (CV) of fine tuned IC parameters following HME and CES tuning. The results were averaged across the three tuned gait phases, then averaged across three subjects (AB1, AB2, and TF1).

The coefficient of variation (CV) in fine-tuned IC parameters following both HME and CES tuning, averaged across 3 subjects, was shown in FIG. 14. Comparable CV of stiffness (K) was observed between the two tuning methods. The CVs of damping coefficient (C) and equilibrium position ($\theta_E$) were higher after CES tuning than those after HME tuning, but the differences were not statistically significant.

Figure 15:
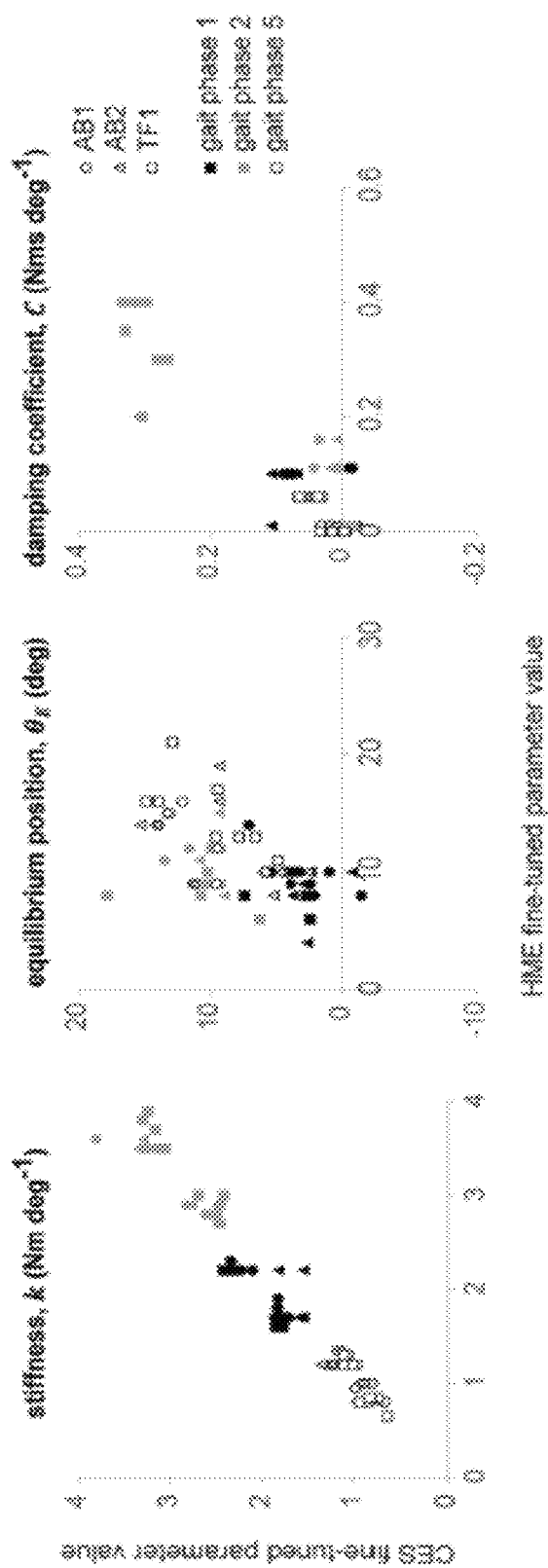
FIG. 15 illustrates fine-tuned IC parameter values from the same initial parameters following HME (x-axis) and CES (y-axis) tuning trials.

FIG. 15 illustrates the fine-tuned IC parameters in all the subjects and all the tuned gait phases. The final values of each IC parameter for each subject and each phase were scattered in a range. The range derived from each of the 3 subjects overlapped one another. Qualitatively, there was relatively poor agreement between CES and HME fine-tuned equilibrium position and damping coefficient values in several trials.

The HME tuning procedure required the subject to take 187.7 strides (SD=76.6), compared to only 96.2 strides (SD=29.8) during CES tuning. HME changed IC parameters on an average of 7 times per trial (SD=2.6), while the CES tuned IC parameters 10.3 times per trial (SD=4.2).

Discussion

Cyber expert system (CES) is a potentially cost-effective approach for tuning impedance control parameters of powered prostheses.

Proficient and cost-effective automatic tuning systems are needed to improve the clinical viability of modern powered prosthetic devices while enabling more natural walking ability. A rule-based CES that automatically tuned the impedance control (IC) parameters of a prototype powered knee prosthesis and closely reproduced an able-bodied knee angle trajectory during level-ground walking is described herein. Compared to manual HME tuning, CES tuning can achieve comparable performance quickly without human expert intervention. Fine-tuning IC parameters with the CES only requires the amputee user to don the powered prosthesis and walk on level ground for several minutes, even outside of the clinical setting, e.g. at home. The CES can then enable the prosthesis to facilitate user adaptation over time by tuning IC parameters either continuously or periodically when initiated by the user. Therefore, the CES can reduce the number of clinical visits and, consequently, healthcare costs for lower limb amputees.

The CES tracked the normative knee trajectory more precisely than the HME by tuning based on quantitative measures rather than qualitative observation. This was observed in all 3 subjects who participated in both the CES and HME tuning trials. Overall, the CES tuning improved or slightly improved gait symmetry and step width in all the subjects. Additionally, the repeatability of CES tuning was comparable to that of HME tuning. However, trunk sway was not reduced after CES tuning as it was following HME tuning, indicating that the human expert's tuning goals may extend beyond the CES's goal of reproducing normative knee joint kinematics. This implication might also be reflected through the relative disagreement between HME and CES fine-tuned IC parameters (FIG. 15). Furthermore, though joint kinematics and impedance of able-bodied subjects have been the target of other powered prosthesis controllers, the additional socket-limb interface, joint mechanics, and segment inertial and geometric properties of current PKPs do not match those of a biological lower limb. Therefore, imposing biological kinematic and dynamic constraints on a non-biological mechanical system may not necessarily elicit natural and optimal gait performance.

Based on tuning results derived from both HME and CES, the fine-tuned IC parameters varied over a range of values, meaning multiple joint impedance values all satisfied the human/cyber expert's tuning criteria. Consequently, there may be no unique optimum parameter solution, and reproducing gait that simply "looks good" might be attainable over a wide range of fine-tuned parameter values. More important optimization criteria may focus on the user's walking function (e.g. walking stability, symmetry, metabolic effort, ability of the human-machine system to reject perturbations) and overall satisfaction.

Though all subjects achieved near normal knee kinematics after tuning, the human expert did not tune IC parameters during the terminal double support (TDS) and swing flexion (SWF) phases. Therefore, the CES likewise did not tune IC parameters during the TDS and SWF phases. The human expert reported difficulty in qualitatively evaluating knee kinematics and walking performance during these phases and, thus, in knowing how to change the IC parameters. In preliminary studies, gait parameters during the TDS and SWF phases show little sensitivity to changes in IC parameters within the range of fine-tuned IC parameter values from previous subjects, suggesting that IC parameter tuning may not be necessary during these phases.

Compared to previous concepts to impose biological joint impedance or incorporate fewer tuned parameters, the CES described herein has shown promising results in this study, and can be directly applied to patients with lower limb amputations. This disclosure contemplates that building a CES based on the knowledge of more experts may further improve the performance of the auto-tuning system for prosthesis control. Further additional or different tuning goals may yield better global gait performance but may require more sensors, leading to other design (electronic components for sensing and communication) and practical (donning extra components on the body) challenges. Formal optimization methods such as "shooting" or "gradient descent" may effectively tune IC parameters without requiring empirical data.

The CES only tuned about half of all configurable parameters in the prosthesis controller (e.g. the low-level IC parameters with each state). Other parameters that could be tuned include those that define transition rules between states, including ground reaction force thresholds distinguishing swing and stance phases, and knee angles and angular velocities distinguishing phases within swing and stance. Three measures of gait performance were evaluated in the example: temporal symmetry, stance width, and trunk sway. Additional criteria for evaluating and rating PKP gait performance, including measures that reflect global human-prosthesis interaction effects, may be desirable (e.g. lower limb joint mechanical power distribution, metabolic cost).

CONCLUSIONS

A cyber expert system (CES) that uses fuzzy logic inference methods to effectively tune the impedance control parameters of a powered knee prosthesis (PKP) during level-ground walking is described herein. While restoring normative knee kinematics generally improved subjects' overall gait performance, greater gains may be achieved by considering additional neural, biomechanical, or energetics measurements in the tuning decisions made by the CES. Given its effectiveness and potential generalizability, the CES is potentially a powerful clinical tool that could make PKPs more practical and accessible for widespread use.

LIST OF SYMBOLS AND ABBREVIATIONS k stiffness
$\theta_E$ equilibrium position
C damping coefficient
$\theta_p$ prosthesis knee joint angle
$\dot{\theta}_p$ prosthesis knee joint angular velocity
$\theta_{peak}$ peak knee angle
$T_{dura}$ gait phase duration
$\dot{\theta}_{peak}$ peak angular velocity
m membership function value
D rule degree
N negative
P positive
CES cyber expert system
HME human expert
CV coefficient of variation'
DF statistical degrees of freedom
GRF ground reaction force
IC impedance control
IDS initial double support
PKP powered knee prosthesis
RMS root-mean-square
SI symmetry index
SS single support
SWE swing extension
SWF swing flexion
TDS terminal double support Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. A system for tuning powered prosthesis impedance control parameters, comprising:
 a powered prosthesis comprising:
  a joint,
  a motor mechanically coupled to the joint, the motor being configured to drive the joint,
  a plurality of sensors configured to measure a plurality of gait parameters associated with a subject, and
  an impedance controller configured to output a control signal for adjusting a torque of the motor;
 an intelligent tuner operably connected to the powered prosthesis, wherein the intelligent tuner is configured to implement an intelligent computing algorithm for adjusting at least one of a plurality of impedance control parameters using a rule base, and wherein the rule base encodes human expert decision making using a plurality of rules that link changes in the measured gait parameters to corresponding adjustments to the impedance control parameters; and
 a finite state machine operably connected to the powered prosthesis, wherein the finite state machine is configured to determine a gait cycle state based on the measured gait parameters and select a set of adjusted impedance control parameters based on the gait cycle state, wherein the impedance controller is configured to adjust the torque of the motor as a function of the measured gait parameters and the set of adjusted impedance control parameters.

2. The system of claim 1, wherein the intelligent tuner is configured to adjust one or more of the impedance control parameters to achieve a target gait characteristic.

3. The system of claim 2, wherein the target gait characteristic is a gait characteristic of a non-disabled subject.

4. The system of claim 1, wherein the changes in the measured gait parameters comprise a respective difference between each of the measured gait parameters and a respective target gait parameter.

5. The system of claim 1, wherein the rule base comprises a respective set of rules for each of the impedance control parameters.

6. The system of claim 1, wherein the rule base comprises a respective set of rules for each of a plurality of gait cycle states.

7. The system of claim 6, wherein the intelligent tuner is configured to adjust the at least one of the impedance control parameters associated with each of the gait cycle states.

8. The system of claim 1, wherein the gait cycle state is selected from a plurality of level ground walking gait cycle states.

9. The system of claim 1, wherein the powered prosthesis further comprises a computing device configured to receive the measured gait parameters and determine one or more gait events.

10. The system of claim 1, wherein the intelligent tuner comprises a fuzzy logic tuner.

11. The system of claim 1, wherein the measured gait parameters comprise at least one of a joint angle, a joint angular velocity, a duration of a gait cycle state, or a load applied to the joint.

12. The system of claim 1, wherein the impedance control parameters comprise at least one of a stiffness, an equilibrium position, or a damping coefficient.

13. The system of claim 1, wherein the joint comprises at least one of a prosthetic knee joint, a prosthetic ankle joint, or a prosthetic hip joint.

14. A computer-implemented method for tuning impedance control parameters of a powered prosthesis, the powered prosthesis comprising a joint, a motor mechanically coupled to the joint, a plurality of sensors, and an impedance controller, the computer-implemented method comprising:
 receiving a plurality of gait parameters associated with a subject from at least one of the sensors;

using an intelligent tuner to adjust at least one of a plurality of impedance control parameters of the powered prosthesis using a rule base, wherein the intelligent tuner is configured to implement an intelligent computing algorithm;

using a finite state machine to determine a gait cycle state based on the measured gait parameters and select a set of adjusted impedance control parameters based on the gait cycle state;

transmitting the set of adjusted impedance control parameters to the powered prosthesis, wherein the rule base encodes human expert decision making using a plurality of rules that link changes in the gait parameters to corresponding adjustments to the impedance control parameters; and using the impedance controller to output a control signal for adjusting a torque of the motor, wherein the torque is adjusted as a function of the gait parameters and the set of adjusted impedance control parameters.

15. The computer-implemented method of claim 14, further comprising adjusting one or more of the plurality of impedance control parameters to achieve a target gait characteristic.

16. The computer-implemented method of claim 14, wherein the rule base comprises a respective set of rules for each of the impedance control parameters or a respective set of rules for each of a plurality of gait cycle states.

17. The computer-implemented method of claim 14, wherein the gait parameters comprise at least one of a joint angle, a joint angular velocity, a duration of a gait cycle state, a load applied to the joint, or a trunk orientation.

18. The computer-implemented method of claim 14, wherein the impedance control parameters comprise at least one of a stiffness, an equilibrium position, or a damping coefficient.

* * * * *